Figure 1:
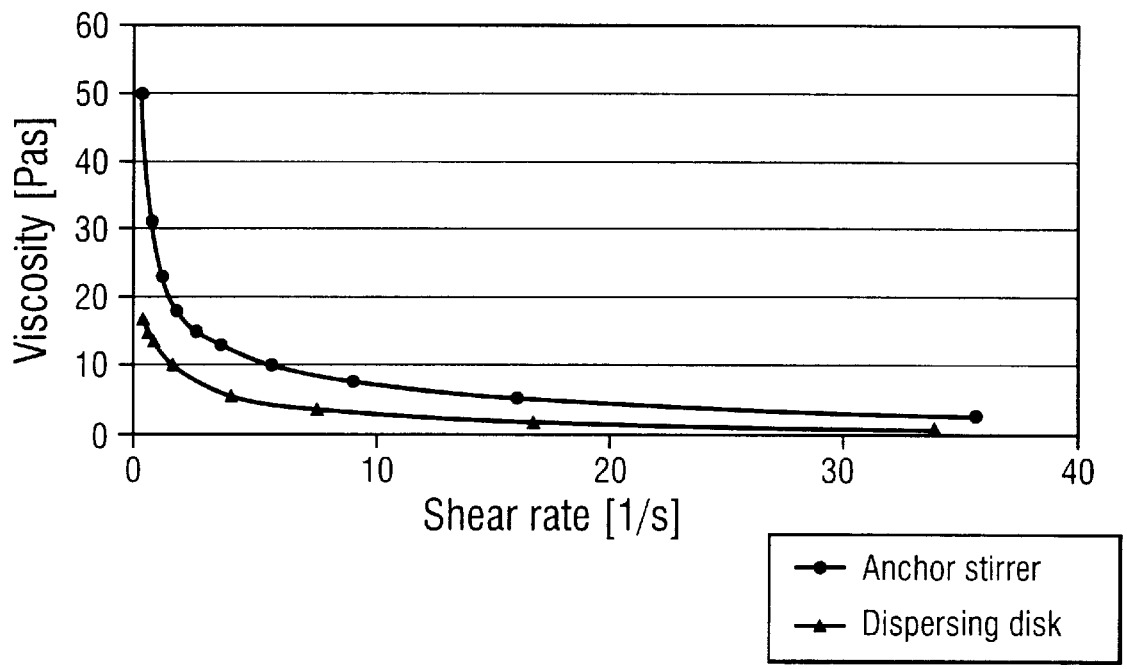

United States Patent
Tittel et al.

[11] Patent Number: 5,840,941
[45] Date of Patent: Nov. 24, 1998

[54] PROCESS FOR THE PREPARATION OF FLOWABLE, ANHYDROUS ACYLOXYALKANESULFONATES AND THEIR USE

[75] Inventors: Viliam Tittel, Hofheim; Dirk Bühring, Frankfurt am Main, both of Germany

[73] Assignee: Hoechst Aktiengesellschaft, Frankfurt, Germany

[21] Appl. No.: 646,879

[22] Filed: May 8, 1996

[30] Foreign Application Priority Data

May 9, 1995 [DE] Germany .................... 195 16 865.8

[51] Int. Cl.$^6$ ............................................. C11D 1/28
[52] U.S. Cl. ............................. 554/92; 554/88; 554/97; 252/544; 252/546
[58] Field of Search ................. 584/85; 252/544, 252/546

[56] References Cited

U.S. PATENT DOCUMENTS 5,384,421  1/1995  Day et al. ...................... 554/92

*Primary Examiner*—Gary Geist
*Assistant Examiner*—Deborah D. Carr
*Attorney, Agent, or Firm*—Miles B. Dearth

[57] ABSTRACT

Process for the preparation of flowable, anhydrous acyloxyalkanesulfonates and their use In the process of the invention, in the context of the esterification of fatty acids with hydroxyalkanesulfonates, the reaction product (molten mass) at 180° to 250° C. is sheared in such a manner during the cooling to 150° to 50° C. that the mean particle size of the product is <100 μm. The acyloxyalkanesulfonate product thus obtained is still highly flowable, pumpable and the like, even at temperatures in the range from 60° to 100° C. and be stored in the fluid state without change at these temperature even over a long period.

8 Claims, 3 Drawing Sheets

PROCESS FOR THE PREPARATION OF FLOWABLE, ANHYDROUS ACYLOXYALKANESULFONATES AND THEIR USE

DESCRIPTION

Process for the preparation of flowable, anhydrous acyloxyalkanesulfonates and their use The invention relates to a process for the preparation of flowable, anhydrous acyloxyalkanesulfonates by esterification of fatty acids with hydroxyalkanesulfonates and their use for the preparation of soaps.

Acyloxyalkanesulfonates are valuable anionic surfactants, which are primarily used for the preparation of syndet soaps, cosmetics and cleaning formulations. They are advantageously prepared by esterification of at least one fatty acid with at least one hydroxyalkanesulfonate (direct esterification). A process of this type is described, for example, in EP-A-0 585 071 (U.S. Pat. No. 5,384,421), in which the fatty acid and the salt of the hydroxyalkanesulfonic acid are reacted in the presence of an esterification catalyst at a temperature of 180° to 240° C. with simultaneous removal of any water present. The reaction product (in the form of a melt) is fluid at temperatures down to about 150° C. In order to obtain a product which is still flowable even at a relatively low temperature, the reaction product is first admixed with fatty acid and adjusted to a pH of 6 to 7. The neutral mixture is then combined with water in an amount of 25 to 90% by weight. The acyloxyalkanesulfonate obtained as aqueous solution or dispersion is then pumpable down to about 50° C. and can also be stored in fluid form at about 50° C.

Pumpable products of acyloxyalkanesulfonates are also described in WO-A-93/16155. They essentially comprise 20 to 60% acyloxyalkanesulfonate, 2 to 50% paraffin, 20 to 55% water, 0 to 7% hydroxyalkanesulfonate and, if appropriate, 5 to 25% fatty acid. They are prepared by a) heating the paraffin and, if appropriate, the fatty acid to or above their melting point, b) adding the acyloxyalkanesulfonate, the water and, if appropriate, the hydroxyalkanesulfonate to the mixture a) and c) cooling the composition to a temperature of 38° to 71° C., the composition being continuously stirred at a high shear rate until the particle size is less than 50 μm. The product thus obtained containing 20 to 55% water is fluid and pumpable down to about 50° C.

Acyloxyalkanesulfonate products which flow well, that is are highly flowable, pourable, pumpable and the like, have the advantage of improved handling. However, the use of water for this purpose is accompanied by a number of disadvantages. Thus, the water leads to an increase in the transport costs, since it is not a valuable material. In many further processing operations of the aqueous acyloxyalkanesulfonate solutions to give finished products, the water must be removed again, in the preparation of syndet soaps, for example. The water can also lead to the acyloxyalkanesulfonate hydrolyzing.

The object of the invention is therefore to propose a process by which, without use of water or other solvents, acyloxyalkanesulfonate products having a high content of active substance are obtained which flow well at relatively low temperatures and, in the fluid state, are also storable and storage-stable, inter alia, also with respect to hydrolysis and phase separation.

The process according to the invention for the preparation of flowable, anhydrous acyloxyalkanesulfonates by esterification of fatty acids with hydroxyalkanesulfonates comprises reacting at least one fatty acid of the formula 1 RCOOH (1), in which R is a hydrocarbon radical having 5 to 31 carbon atoms, with at least one hydroxyalkanesulfonate of the formula 2 HO—$R^1$—$SO_3X$ (2), in which $R^1$ is a $C_2$- to $C_4$-alkylene or a divalent di-$C_2$- to $C_4$alkylether radical and X is an alkali metal or ammonium, in the presence of an esterification catalyst at a temperature of 180° to 250° C., preferably 190° to 230° C., with removal of the water present, cooling the reaction product to a temperature of 150° to 50° C., preferably 110° to 60° C., and shearing the mixture during cooling in such a manner that the mean particle size of the product is less than 100 μm.

Acyloxyalkanesulfonate crystallizes even at elevated temperatures in the form of needle-shaped crystals, which produces a mass which is matted together and particularly solid. The invention is based on the surprising observation that this can be prevented and a product which is still flowable and pumpable even at relatively low temperatures is obtained, without use of water or other solvents or dispersants, if, during said cooling, the structure of the crystal mass is destroyed and the needle-shaped crystals are reduced in size and their morphology is altered. The product, which is then to have a mean particle size of <100 μm, is still highly pourable, pumpable and the like, even at temperatures in the range from about 60° to 100° C. and is storable in the fluid state without change at this temperature even over a relatively long period.

In the process of the invention, the reaction product at 180° to 250° C., preferably 190° to 230° C., after it reaches the sought-after degree of conversion, is cooled to a temperature of 150° to 50° C., preferably 110° to 60° C., for example by continuous cooling of the reaction vessel (jacket cooling). During the entire cooling phase, which generally lasts for 2 to 6 hours, the mass is subjected to shear forces such that its mean particle size, after the said temperature in the range from 150° to 50° C., preferably 110° to 60° C., is reached, is below 100 μm, preferably about 10 to 80 μm. The required high shearing is achieved, for example, using mixing, stirring or homogenizing devices, such as dispersing disks, homogenizers, cavitron apparatuses, rotor-stator mixers and the like. In the reaction phase, that is from the beginning of the reaction to the achievement of the desired degree of conversion and the initiation of the cooling phase, the conventional agitation of the melt is sufficient, for example using a standard anchor stirrer. To avoid exchanging a conventional stirrer for a shearing device, it can be expedient to use the shearing device as early as at the start of the reaction. It is critical that said shearing is performed in the cooling phase. The acyloxyalkanesulfonate product thus obtained has the specified properties with respect to flowability at temperatures down to about 100° to 60° C.

The reaction of the invention of fatty acid and hydroxyalkanesulfonate is performed in the presence of a catalyst. Suitable esterification catalysts are described extensively in said EP-A-0 585 071, which is herein incorporated by reference. These are alkanesulfonic acids, hydroxyalkanesulfonic acids, arylsulfonic acids, inorganic acids such as sulfuric acid, phosphoric acid, phosphorous acid, boric acid or anhydrides thereof, heavy metal salts such as zinc sulfate, zirconium sulfate, zinc isethionate, zinc borate, aluminum sulfate, titanium sulfate or tungsten phosphate, metal oxides such as zinc oxide, aluminum oxide, magnesium oxide, cerium oxide, zirconium oxide or lanthanum oxide, in addition mixtures of 2 or more of said catalysts, and soaps which are formed from heavy metals and metal oxides. A particularly preferred esterification catalyst is zinc oxide.

The esterification catalyst is used in an amount of generally 0.05 to 2% by weight, preferably 0.05 to 1% by weight, percentages by weight being based on fatty acid and hydroxyalkanesulfonic salt.

The reaction of fatty acid and hydroxyalkanesulfonic acid salt, generally in a molar ratio of 1:1 to 2:1, preferably about 1:1, is carried out according to the invention at a temperature of 180° to 250° C. The preferred temperature range is 190° to 230° C. The water possibly introduced into the reaction mixture with the starting components and the water formed by the esterification reaction is continuously discharged from the reaction mixture. The reaction mixture, under some circumstances, can be highly viscous to a greater or lesser extent. In such cases, so-called consistency regulators are used, special fatty acids and/or paraffins, for example, as are described in EP-A-0 585 071. The time up to the sought-after conversion rate is about 4 to 8 hours. Generally, the cooling of the melt and termination of the esterification reaction are begun at a conversion rate of about 50 to 80% by weight acyloxyalkanesulfonate (active substance).

The process of the invention, in detail, can be carried out, for example, in such a manner that, at atmospheric pressure, the fatty acid, the salt of the hydroxyalkanesulfonic acid and the esterification catalyst are introduced into a reaction vessel and the mixture is heated to the specified temperature with stirring. Water present distills off as early as during the heating of the reaction mixture and then continuously distills off during the running esterification reaction. The process of the invention can also be carried out by the method described in EP-A-0 585 071. Here, the esterification reaction is carried out partly at atmospheric pressure and partly under vacuum for more rapid discharge of the water. After the sought-after degree of conversion has been achieved, the product is cooled as described above and treated by the action of shear forces. It then has the said particle size and is also still highly flowing and storable in the fluid state in the range from 60° to 100° C. The product becomes solid with further cooling. The solid product can be further processed for formulation using, for example, a flaking roller or a cooling belt.

The following may be further stated with reference to the starting compounds fatty acid and hydroxyalkanesulfonate: in the fatty acid RCOOH, R is a hydrocarbon radical having 5 to 31 carbon atoms which can be saturated or unsaturated, linear or branched. R can also be a mixture of such hydrocarbon radicals. R is preferably $C_5$- to $C_{21}$alkyl or $C_5$- to $C_{21}$-alkenyl or a mixture thereof. The alkenyl radicals are preferably monounsaturated to triunsaturated. Examples which may be mentioned are caproic acid, capric acid, lauric acid, myristic acid, stearic acid, arachic acid, oleic acid, linoleic acid, linolenic acid, coconut acid and tallow acid and mixtures thereof. The branched hydrocarbon radical R is preferably a radical of the formula 1a below

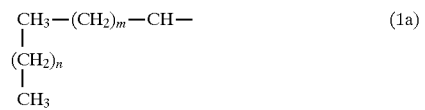
(1a)

in which m is an integer from 4 to 18, preferably 4 to 14, and n is 0 or an integer from 1 to 10, preferably 0 or an integer from 1 to 6. Fatty acids of this type therefore correspond to the formula 1b below

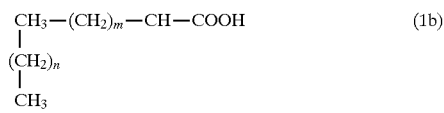
(1b)

in which m and n have the meanings given above. Examples of branched fatty acids are: 2-ethylhexanoic acid, 2-pentyloctanoic acid, 2-butylnonanoic acid, 2-propyldecanoic acid, 2-ethylundecanoic acid, 2-butylundecanoic acid, 2-methyldodecanoic acid, 2-ethyltridecanoic acid and 2-methyltetradecanoic acid and mixtures thereof.

Preferred hydroxyalkanesulfonates HO—$R^1$—$SO_3X$ are those in which $R^1$ is —$CH_2CH_2$—, —$(CH_2)_3$—, —$CH_2CH(CH_3)$— or —$CH_2CH_2OCH_2CH_2$—, ethylene being particularly preferred, and the counter ion X is $NH_4$ or an alkali metal, preferably sodium or potassium. The salt of hydroxyalkanesulfonic acids particularly preferred according to the invention is potassium isethionate, sodium isethionate or ammonium isethionate. The hydroxyalkanesulfonic salts can be used as such; preferably they are used in the form of an aqueous solution, generally as 40 to 65% strength by weight solution.

The anhydrous acyloxyalkanesulfonate products prepared according to the invention, which can be transported without problems, for example in heated road tankers, are preferably used for the preparation of syndet soaps. They are especially suitable for this because they can be further processed as such (they contain no water or other solvents and foreign components which would have to be removed in advance) and because, owing to their fine particle size, they give soaps having a particularly smooth surface.

The process of the invention can also be carried out on an industrial scale. Owing to the direct esterification (direct condensation), the use of fatty acid chlorides can be avoided, which would otherwise have to be prepared from fatty acid in a separate step. The acyloxyalkanesulfonate products obtained according to the invention have, as further advantageous properties, in addition to the abovedescribed, good water solubility and hard water stability, high foam formation and good skin tolerance. The anhydrous melts prepared according to the invention generally contain, as mentioned above, 50 to 80% by weight of acyloxyalkanesulfonate (active substance), based on the solid or fluid total product. The acyloxyalkanesulfonate corresponds to the formula 3 below

(3)

in which R, $R^1$ and X have the meanings given above.

The invention is now described in more detail with reference to Examples (according to the invention) and comparison examples (not according to the invention) Percentages are by weight, unless stated otherwise.

COMPARISON EXAMPLE 1

876 g of coconut acid, 776 g of aqueous sodium isethionate solution (57%) and 2.4 g of zinc oxide are introduced into a 3 l flat flange reaction vessel having an anchor stirrer, descending vertical recovery bend, internal thermometer and nitrogen feed line. The mixture is heated to 220° C. and the solution water of the sodium isethionate and the water formed in the direct condensation is distilled off. At a sodium cocoylisethionate content of 75%, 147 g of paraffin, 178 g of stearic acid, 78 g of lauric acid and 78 g of polyethylene glycol 2000 are added and the molten mass is cooled with stirring to 67° C. It is then stored at 80° C. After storage for 2 days, the product is still flowable. It is then heated to 150° C. and then cooled to 80° C. without stirring, becoming solid after a short time.

COMPARISON EXAMPLE 2

876 g of coconut acid, 776 g of aqueous sodium isethionate solution (57% strength) and 2.2 g of zinc oxide are introduced into a 3 l flat flange reaction vessel having an anchor stirrer, descending vertical recovery bend, internal thermometer and nitrogen feed line. The batch is heated to 230° C. and the solution water of the sodium isethionate and the water formed in the direct condensation is distilled off. At a sodium cocoylisethionate content of 78%, 750 g of paraffin and 140 g of stearic acid are added and the mixture is cooled to 80° C. with stirring and stored at this temperature. After storage for 3 days, the product is pasty and cannot be completely poured out of the flat flange reaction vessel.

EXAMPLE 1

The procedure as in Comparison Example 2, a dispersing disk being used instead of the anchor stirrer. In contrast to Comparison Example 2, the product, which has a particle size of about 80 μm on average, is still a mobile fluid even after storage for 14 days at 80° C., and may be poured out completely from the flat flange reaction vessel.

Figure 2:
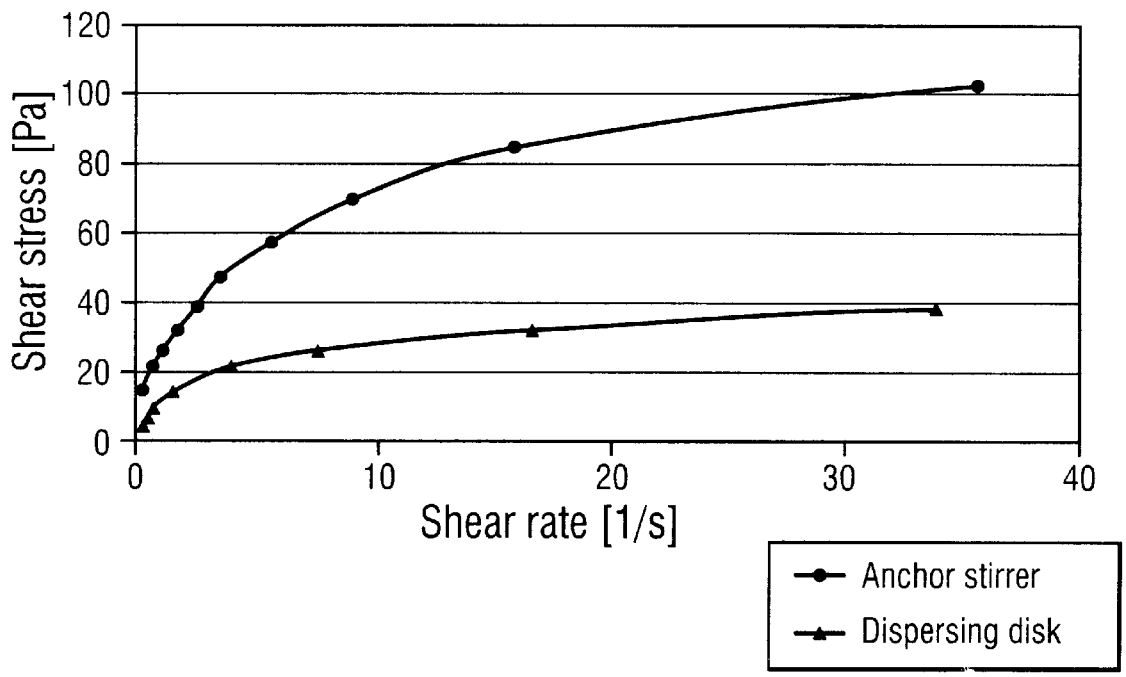

FIGS. 1 and 2 show the flow curves of the two products.

COMPARISON EXAMPLE 3

876 g of coconut acid, 776 g of aqueous sodium isethionate solution (57%) and 2.2 g of zinc oxide are introduced into a 3 l flat flange reaction vessel having an anchor stirrer, descending vertical recovery bend, internal thermometer and nitrogen feed line. The batch is heated to 230° C. and the solution water of the sodium isethionate and the water formed in the direct condensation is distilled off. At a sodium cocoylisethionate content of 78%, 470 g of paraffin and 210 g of stearic acid are added and the melt is cooled to 80° C. with stirring and stored at this temperature. After storage for 1 day, the product is pasty and cannot be poured out of the flat flange reaction vessel

EXAMPLE 2

The procedure as in Comparison Example 3, a dispersing disk being used instead of the anchor stirrer. In contrast to Comparison Example 3, the product, which has a mean particle size of about 50 μm, is a mobile fluid even after storage for 14 days at 60° C. and may be poured out completely from the flat flange reaction vessel.

Figure 3:
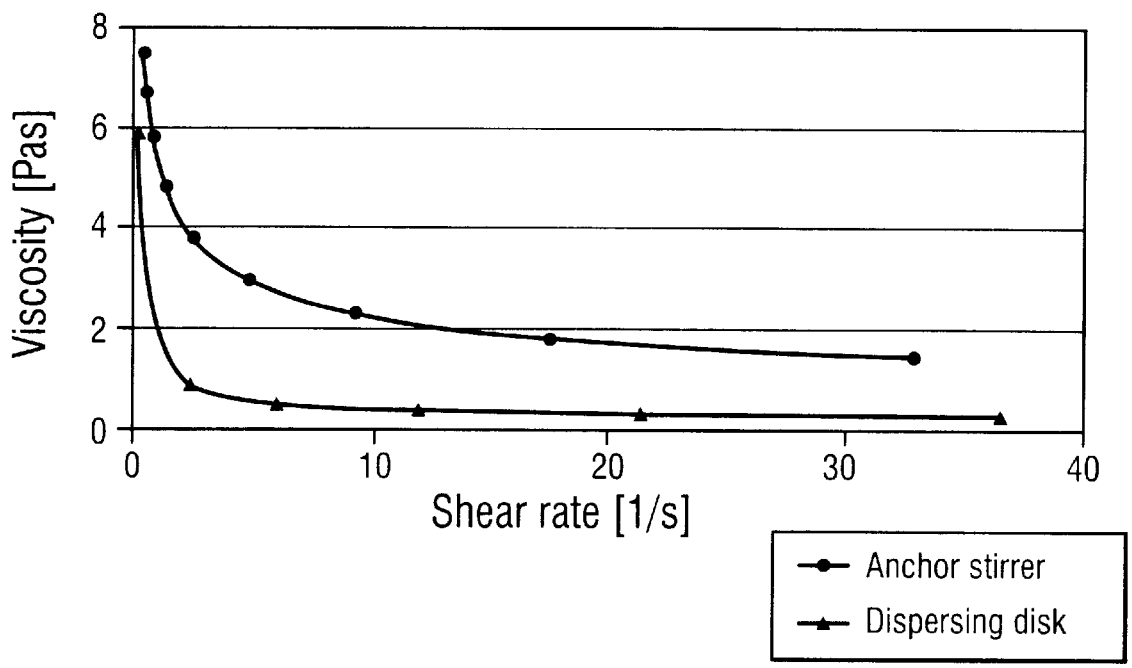
Figure 4:
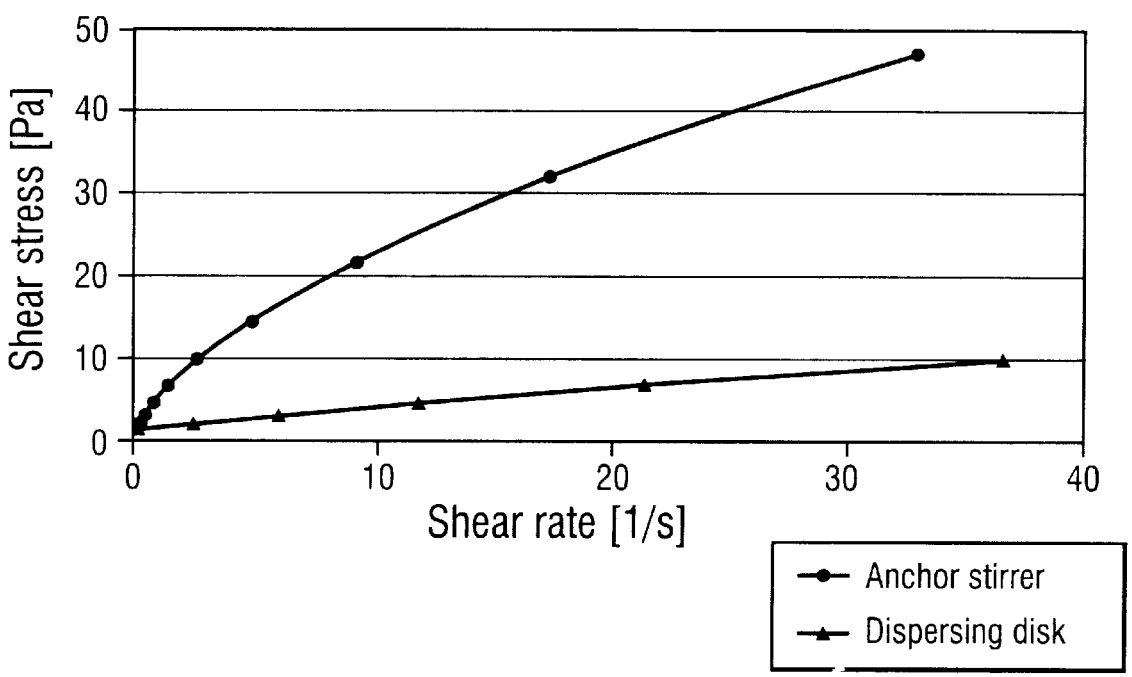

FIGS. 3 and 4 show the flow curves of the two products.

EXAMPLE 3

533 g of coconut acid, 511 g of aqueous sodium isethionate solution (57%) and 1.6 g of zinc oxide are introduced into a 3 l flat flange reaction vessel having a dispersing disk as stirring and mixing device, a descending vertical recovery bend, internal thermometer and nitrogen feed line. The batch is heated to 230° C. and the solution water of the sodium isethionate and the water formed in the direct condensation is distilled off. At a sodium cocoylisethionate content of 77%, about 40 g of the coconut acid used in excess are distilled off and then 187 g of stearic acid are added and the melt is cooled to 95° C. with stirring. The product remained a pumpable paste over the period of 6 days at a storage temperature of about 100° C.

Figure 5:
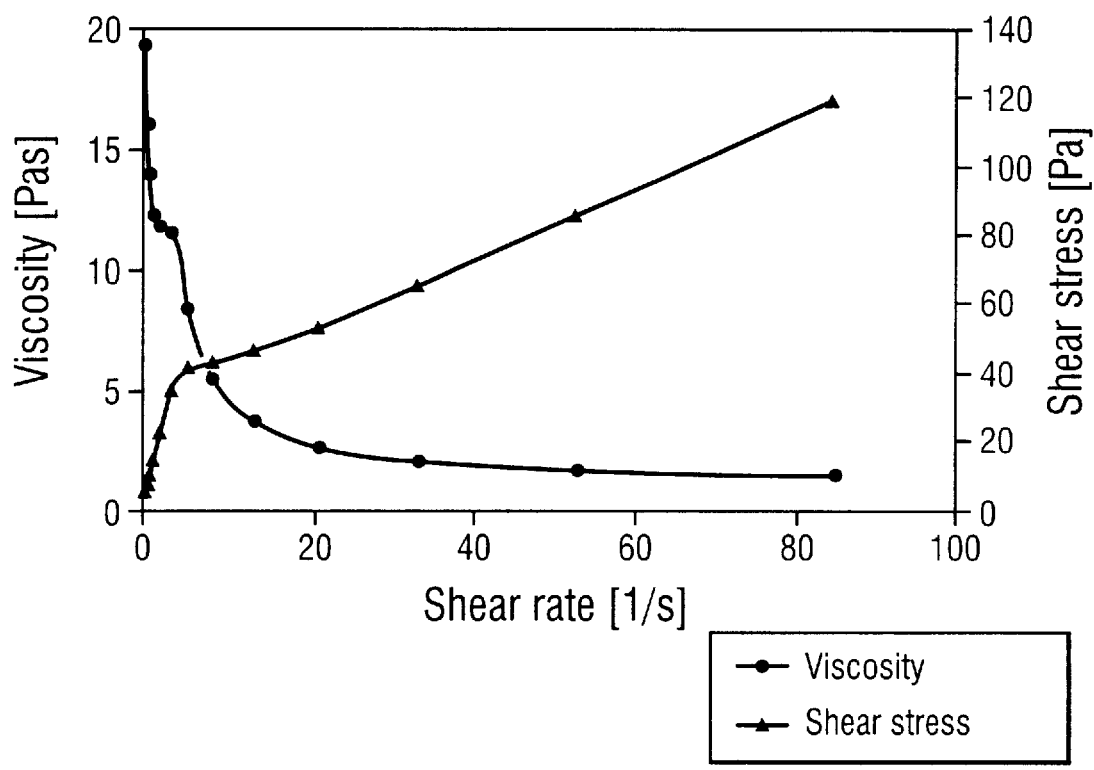

If the product is not prepared with a dispersing disk, but with an anchor stirrer, it solidifies at about 140° C. The flow curve is shown in FIG. 5.

EXAMPLE 4

63 kg of hydroxyethanesulfonate solution, 65 kg of coconut acid, 6 kg of lauric acid and 0.2 kg of zinc oxide powder are introduced into a 360 l stirred tank having an anchor stirrer, descending distillation head, nitrogen feed line and temperature measurement in the vessel and are then heated to 220° C. with distillation of water. After condensation is completed, 40 kg of paraffin are added and the melt is cooled to 150° C. with circulation by pumping through a cavitron apparatus. At this temperature, 14 kg of stearic acid are added and the melt is then cooled to 80° C. with further circulation by pumping through the cavitron apparatus and charged from the vessel into drums. The product is stored at 80° C. for a plurality of days, remaining pumpable and flowable.

COMPARISON EXAMPLE 4

Procedure similar to Example 4, circulation device comprising circulation pump and cavitron apparatus are not switched on during the cooling. In this case, even after only a few hours at 80° C., the product is solid and no longer flowable.

We claim:

1. A process for the preparation of flowable, anhydrous acyloxyalkanesulfonates by esterification of fatty acids with hydroxyalkanesulfonates, which comprises reacting at least one fatty acid of the formula 1 RCOOH (1), in which R is a hydrocarbon radical having 5 to 31 carbon atoms, with at least one hydroxyalkanesulfonate of the formula 2 HO—$R^1$—$SO_3$X (2), in which $R^1$ is a $C_2$- to $C_4$-alkylene or a divalent di-$C_2$- to $C_4$-alkylether radical and X is an alkali metal or ammonium, in the presence of an esterification catalyst at a temperature of 180° to 250° C. with removal of the water present, cooling the reaction product to a temperature of 150° to 50° C. and shearing the mixture during cooling in such a manner that the mean particle size of the product is less than 100 μm.

2. The process as claimed in claim 1, wherein R is a linear or branched alkyl radical having 5 to 21 carbon atoms or a linear or branched alkenyl radical having 5 to 21 carbon atoms or a mixture thereof, $R^1$ is —$CH_2CH_2$—, —$(CH_2)_3$—, —$CH_2CH(CH_3)$— or —$CH_2CH_2OCH_2CH_2$— and X is sodium, potassium or ammonium.

3. The process as claimed in claim 1, wherein the reaction is carried out at a temperature of 190° to 230° C.

4. The process as claimed in claim 1, wherein the fatty acid and the hydroxyalkanesulfonate are used in a molar ratio of 1:1 to 2:1.

5. The process as claimed in claim 1, wherein the esterification catalyst used is zinc oxide in an amount of 0.05 to 2% by weight, based on fatty acid and hydroxyalkanesulfonate.

6. The process as claimed in claim 1, wherein the reaction product is cooled to a temperature of 110° to 60° C.

7. The process as claimed in claim 1, wherein, during the cooling, shearing is carried out in such a manner that the mean particle size of the product is 10 to 80 μm.

8. The process as claimed in claim 1, wherein at least one fatty acid of the formula 1, in which R is a linear or branched alkyl radical having 5 to 21 carbon atoms or a linear or branched alkenyl radical having 5 to 21 carbon atoms or a mixture thereof, is reacted with at least one hydroxyalkanesulfonate of the formula 2, in which $R^1$ is —$CH_2CH_2$—, —$(CH_2)_3$—, —$CH_2CH(CH_3)$— or —$CH_2CH_2OCH_2CH_2$— and X is sodium, potassium or ammonium, in a molar ratio of 1:1 to 2:1 in the presence of zinc oxide in an amount of 0.05 to 2% by weight, based on fatty acid and hydroxyalkanesulfonate, at a temperature of 180° to 250° C., the reaction product is cooled to a temperature of 150° to 50° C. and sheared in such a manner during the cooling that the mean particle size of the product is less than 100 μm.

* * * * *